(12) United States Patent
Toporek

(10) Patent No.: US 12,214,175 B2
(45) Date of Patent: Feb. 4, 2025

(54) ELECTRONIC-INK LABEL FOR A DRUG DELIVERY DEVICE

(71) Applicant: Sanofi, Paris (FR)

(72) Inventor: Maurice Toporek, Frankfurt am Main (DE)

(73) Assignee: Sanofi, Paris (FR)

( * ) Notice: Subject to any disclaimer, the term of this patent is extended or adjusted under 35 U.S.C. 154(b) by 855 days.

(21) Appl. No.: 17/294,533

(22) PCT Filed: Nov. 19, 2019

(86) PCT No.: PCT/EP2019/081715
§ 371 (c)(1),
(2) Date: May 17, 2021

(87) PCT Pub. No.: WO2020/104410
PCT Pub. Date: May 28, 2020

(65) Prior Publication Data
US 2022/0016353 A1    Jan. 20, 2022

(30) Foreign Application Priority Data
Nov. 23, 2018 (EP) .................................. 18306561

(51) Int. Cl.
*A61M 5/315* (2006.01)
*A61M 5/20* (2006.01)
*A61M 5/31* (2006.01)

(52) U.S. Cl.
CPC .......... *A61M 5/31568* (2013.01); *A61M 5/20* (2013.01); *A61M 5/31511* (2013.01);
(Continued)

(58) Field of Classification Search
CPC ...... A61M 2005/3126; A61M 5/31546; A61M 5/31568; A61M 2205/3317;
(Continued)

(56) References Cited

U.S. PATENT DOCUMENTS 7,935,088 B2    5/2011 Veasey et al.
2015/0302818 A1    10/2015 Cowe et al.
(Continued)

FOREIGN PATENT DOCUMENTS

WO    WO 2010/098928    9/2010
WO    WO 2014/111338    7/2014
(Continued)

OTHER PUBLICATIONS

International Preliminary Report on Patentability in International Application No. PCT/EP2019/081715, dated May 25, 2021, 9 pages.
(Continued)

*Primary Examiner* — Emily L Schmidt
*Assistant Examiner* — Samuel J Marrison
(74) *Attorney, Agent, or Firm* — Bond, Schoeneck & King, PLLC

(57) ABSTRACT

Described is an indication system for a drug delivery device, including a component moveable with respect to a housing during operation of the drug delivery device, an electric circuit having an electrical property, and an electronic-ink label configured to be disposed on the exterior of the housing and in contact with the electric circuit. The electric circuit is operatively coupled to the moveable component to modify the electrical property based on a position of the moveable component such that the electrical property is an indication of the position of the moveable component. The electronic ink label includes printed electronics arranged to be in communication with the electric circuit and configured to display a visual indication related to the position of the moveable component in response to the electrical property. In some instances, the position of the moveable component indicates a dose set or dispensed from the drug delivery device.

12 Claims, 10 Drawing Sheets

(52) U.S. Cl.
CPC .............. *A61M 2005/3126* (2013.01); *A61M 2205/3317* (2013.01); *A61M 2205/3553* (2013.01); *A61M 2205/8206* (2013.01)

(58) Field of Classification Search
CPC .... A61M 2205/502; A61M 2205/6027; A61M 5/31565; A61M 5/31566; A61M 5/3157
See application file for complete search history.

(56) References Cited

U.S. PATENT DOCUMENTS

| | | | |
|---|---|---|---|
| 2016/0136353 A1* | 5/2016 | Adams | A61M 5/1458 604/152 |
| 2016/0263327 A1* | 9/2016 | Radmer | G16H 20/10 |
| 2017/0138769 A1* | 5/2017 | Jones | A61M 5/31553 |
| 2020/0030542 A1* | 1/2020 | Jakobsen | A61M 5/31551 |
| 2021/0077736 A1* | 3/2021 | Larsen | G09F 3/02 |

FOREIGN PATENT DOCUMENTS

| | | | | |
|---|---|---|---|---|
| WO | WO 2014/111341 | 7/2014 | | |
| WO | WO 2014/111342 | 7/2014 | | |
| WO | WO-2014173768 A1 * | 10/2014 | ........... | A61B 90/361 |
| WO | WO-2016055620 A1 * | 4/2016 | .............. | A61M 5/20 |
| WO | WO 2017/016959 | 2/2017 | | |
| WO | WO-2018111709 A1 * | 6/2018 | .......... | A61M 5/2422 |
| WO | WO 2019/121616 | 6/2019 | | |

OTHER PUBLICATIONS

PCT International Search Report and Written Opinion in International Application No. PCT/EP2019/081715, dated Jan. 2, 2020, 13 pages.

* cited by examiner

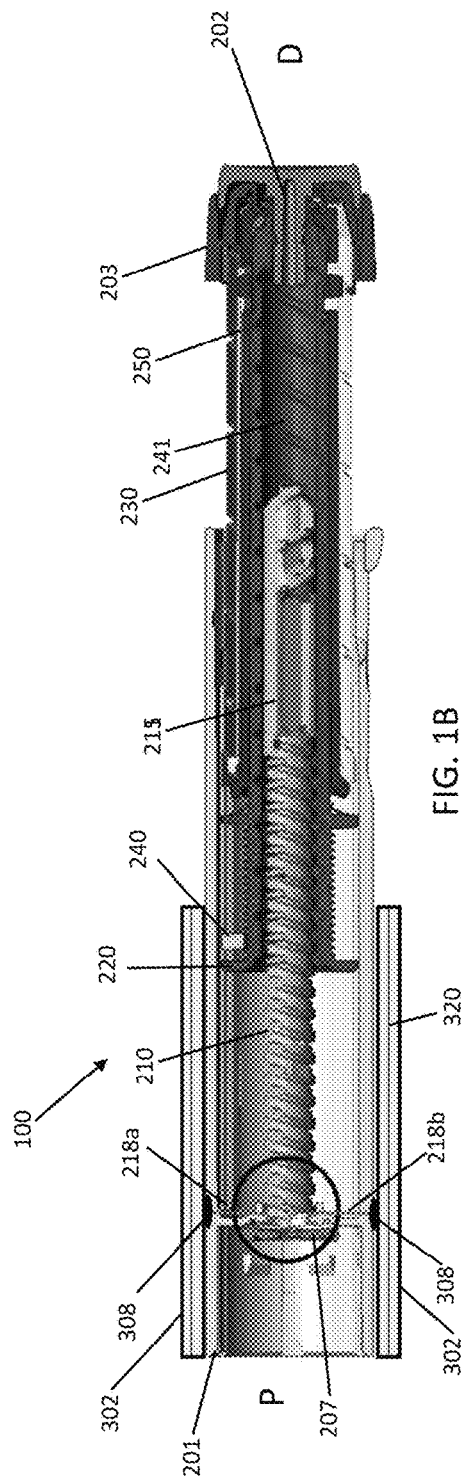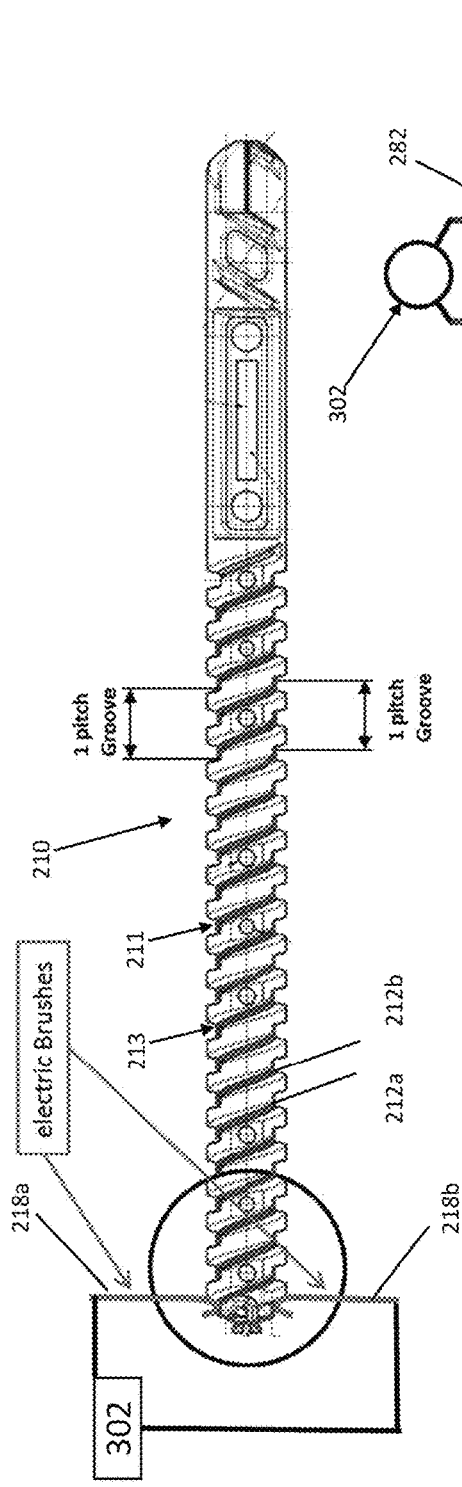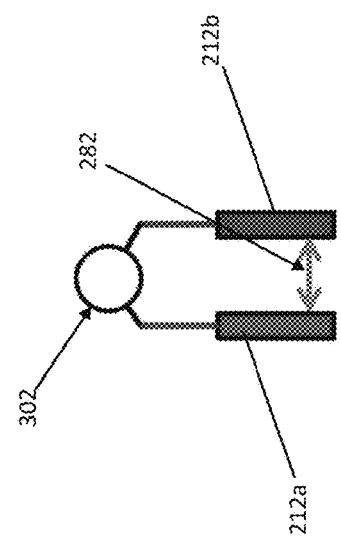
FIG. 1B
FIG. 2A
FIG. 2B

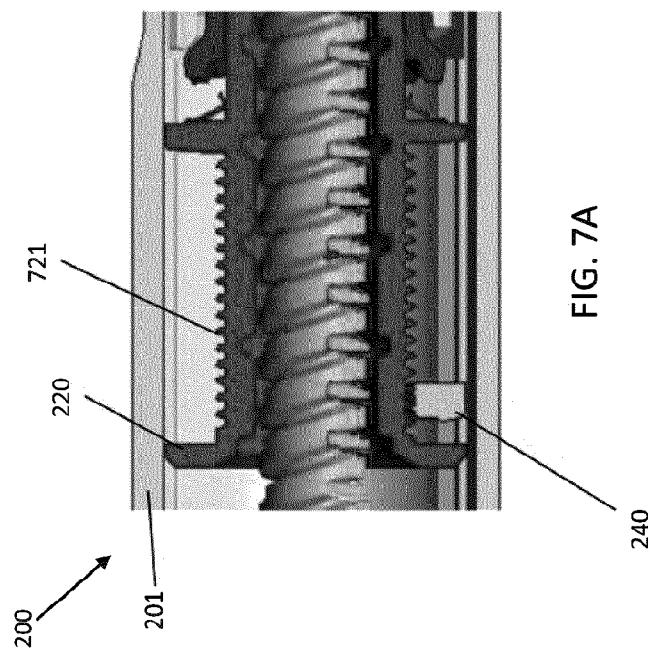

ELECTRONIC-INK LABEL FOR A DRUG DELIVERY DEVICE

CROSS REFERENCE TO RELATED APPLICATIONS

The present application is the national stage entry of International Patent Application No. PCT/EP2019/081715, filed on Nov. 19, 2019, and claims priority to Application No. EP 18306561.4, filed on Nov. 23, 2018, the disclosures of which are incorporated herein by reference.

TECHNICAL FIELD

This description relates to an electronic-ink label for providing a visual indication of a status (e.g., fill level) of a drug delivery device.

BACKGROUND

A variety of diseases can be treated by injection of a medicament. Such injections can be performed using drug delivery devices, which can be applied either by medical personnel or by patients themselves. As an example, type-1 and type-2 diabetes can be treated by patients themselves by injection of drug doses, for example once or several times per day. For instance, a pre-filled disposable drug pen or autoinjector can be used as a drug delivery device. Alternatively, a re-usable pen or autoinjector may be used. A re-usable pen or autoinjector allows replacement of an empty medicament cartridge (or any other kind of medicament container) by a new one. Either type of pen or autoinjector may come with a set of one-way needles that are replaced before each use. The medicament dose may vary individually, therefore a user (e.g., a patient or health care professional) may select the amount of medicament required (e.g. dial a dose) by operating a dose setting mechanism of the drug delivery device prior to use.

SUMMARY

This disclosure relates to drug delivery devices having an electronic-ink label capable of displaying to a user a status (e.g., fill level or last dose) of the drug delivery device, where the electronic-ink label is in electrical communication with a dose tracking mechanism of the drug delivery device. In operation, the electronic-ink label is in electrical communication with an electric circuit of the dose tracking mechanism and displays a status corresponding to a position of the dose tracking mechanism based on variations in the electric circuit sensed by the electronic-ink label. This principle is based on using an electronic-ink label, which typically includes a printed circuit, an internal power source, and a visual indicator capable of displaying one or more indications. For example, the electronic-ink label can display a current fill level of the drug delivery device, or a dose of medicament that was delivered by the drug delivery device. In operation, the electric circuit of the dose tracking mechanism has an electrical property (e.g., resistance, capacitance, or inductance) that varies according to a position of a moving component of the dose tracking mechanism, and the visual indicator of the electronic-ink label changes in response to a value of the electrical property. In some instances, the electronic-ink label is removeably attached to an exterior of the drug delivery device and makes electrical contact with the electric circuit of the drug delivery device via contact points on the exterior of the drug delivery device.

In a representative example, an electronic-ink label is adhered to an exterior of a housing of a drug delivery device, and the printed electronics of an electronic-ink label is in electrical communication with a variable electronics device inside the drug delivery device, such as a variable resistor or capacitor, where the configuration of the variable electronics device is operatively coupled with the movements of one or more components of the drug delivery device responsible for a dose setting or dispensing operation of the drug delivery device. In this manner, when a position of a component of the drug delivery device (e.g., part of a dose setting mechanism or a dose dispensing mechanism) changes during a dose setting operation or a dose dispensing operation dose, a corresponding change in the configuration of the variable electronics device is sensed by the electronic-ink label. As a result, an indicator on the electronic-ink label changes and this change corresponds to the change in position of the component. In some instances, the change displayed by the indicator of the electronic-ink label is therefore an indication of the fill level of the drug delivery device, a dose set during the dose setting operation, or a dose dispensed during the dose dispensing operation, depending on the function of the moveable components controlling the variable electronics device.

For example, if 10 units of a medicament is delivered from a drug delivery device with a corresponding movement of a dose dispensing mechanism, the variable electronics component is adjusted by an amount corresponding to the 10 units, and this, in turn, causes a change in indication of electronic-ink label to indicate 10 units of medicament being delivered (e.g., with a change in a remaining fill level or an indication of the dose administer). As an illustrative example, an electronic-ink label has an indicator level showing the fill level of the drug delivery device from empty to full, and variable electronics are coupled to a dose memory device such that changing in position of the dose memory mechanism changes the fill level indicator of the electronic-ink label by one unit for every unit of dose dispensed by the drug delivery device by changing a property of the electric circuit of the dose memory mechanism (e.g., resistance, capacitance, or inductance). Therefore, after dispensing 10 units of dose the indicator of the electronic-ink label is changed by 10 units.

Aspects of this system can be implemented in a drug delivery device in a number of ways. In one example, a plunger rod (e.g., a leadscrew) has two conductive wires running down a helical track, and the plunger rod is advanced though a bearing nut during a dose dispensing operation. The two conductive wires are embedded in the helical track and joined at one end of the plunger rod. The bearing nut has two metal brushes contacting the two conductive wires and electronic-ink label has printed electronics connected across the two metal brushes. Therefore, the length of wiring of the electric circuit (e.g., a portion of conductive wiring of the plunger rod defined by the position of the metal brushes) is changed by the position of the plunger rod with respect to the bearing nut. Thus, as the plunger rod is advanced though the bearing nut during a dose dispensing operation, a value of an electrical property of the electric circuit is modified as the length of the electric circuit is changed, and this results in a corresponding change in a visual indication on the electronic-ink label. In another example, a variable resistor is connected to the plunger rod such that rotation of the plunger rod rotates a component of the variable resistor and changes the resistance (i.e., an electrical property), which results in a change in the visual indication on the electronic-ink label corresponding to the change in the position of the plunger rod.

In addition, a medicament and/or dose information can be visible on the electronic-ink label. In some instances, this may be only a unique tag serial number, or may be product-related information such as a stock number, lot or batch number, production date, or other specific information. In some instances, the electronic-ink label includes an RFID chip configured to transmit an electric indication of the position of the moveable components. In some instances, the RFID chip also transmits medicament and/or dose information and/or fill level information. Because RFID chips can have individual serial numbers, aspects of the present RFID tracking mechanism can discriminate among several tags that might be within the range of the RFID reader (i.e., an external device) and read several tags simultaneously. In this manner, it can be ensured that only the correct device is interrogated and the respective response is captured by the RFID reader.

Certain aspects of the present disclosure result in several advantages beyond the ability to easily track a fill level or dispensed dose from a drug delivery device. For example, the electronic-ink label can be adhered to the exterior of the drug delivery device after drug delivery device has completed manufacturing or filling, and the lack of an integrated fill level or dose delivery indicator can reduce the overall cost of the components and construction of the drug delivery device. The electronic-ink label also provides for an electric display means with a low-power consumption, which increase the shelf-life of the electronic-ink label and the drug delivery device. In addition, the inclusion of an RFID chip in an electronic-ink label enables RFID functionality to be easily added to a drug delivery device. Additionally, with existing drug delivery devices, there are only minor modifications required to the dose delivery or setting mechanism to integrate the RFID chip, due to the small size and thickness of typical RFID chips.

An example embodiment of the present disclosure is a dose tracking system for use in a drug delivery device. The dose tracking system includes a housing, a moveable component configured to move with respect to the housing during operation of the drug delivery device, electric circuit with an electric contact on an exterior of the housing, and an electronic-ink label configured to be disposed on the exterior of the housing. The electric circuit defines an electrical property and includes an electrical component operatively coupled to the moveable component and configured to modify the electric property based on a position of the moveable component. The electronic-ink label includes printed electronics arranged to be in electrical communication with the electric circuit via the electric contact and configured to display a visual indication related to the position of the moveable component in response to the electrical property of the electric circuit.

In some instances, the moveable component is configured to move between a plurality of possible positions with respect to the housing, and wherein each of the plurality of positions of the moveable component defines a different value of the electrical property of the electric circuit, such that each value of the electrical property is an indication of a different position of the moveable component.

In some instances, the electrical component is configured to vary an electrical property of the electrical component as a function of the position of the moveable component, wherein the visual indication is configured to be a function of the electrical property varied by the electrical component, and wherein the electrical property is one or more of the following: capacitance, inductance, or resistance.

In some instances, the doses tracking mechanism includes a dose setting mechanism having the moveable component, and wherein the position of the moveable component corresponds to a dose of medicament to be delivered by the drug delivery device as set by the dose setting mechanism, and wherein the visual indication corresponds to the dose of medicament set by the dose setting mechanism.

In some instances, the doses tracking mechanism includes a dose dispensing mechanism having the moveable component, and wherein the position of the moveable component corresponds to a dose of medicament dispensed from the drug delivery device by the dose dispensing mechanism, and wherein the visual indication corresponds to the dose of medicament dispensed from the drug delivery device.

In some instances, the doses tracking mechanism includes a dose memory mechanism having the moveable component, and wherein the position of the moveable component corresponds to a total dose of medicament remaining in the drug delivery device, and wherein the visual indication corresponds to the total dose of medicament remaining in the drug delivery device. In some instances, the electrical component is a variable electronic resistor comprising a conductive electrode disposed in a track along the moveable component.

In some instances, the electrical component is a variable resistor comprising a conductor disposed in a track along the moveable component. In some instances, the track is a first track comprising a first conductor, and the variable resistor comprises a second conductor disposed in a second track along the moveable component.

In some instances the electrical component is a variable resistor including a first component having a track spanning at least a portion of a length of the first component, and first and second conductors along the track, a second component moveable with respect to the first component along the track, the second component contacting the first and second conductors, and an electrical contact between the first and second conductors having resistance proportional to a position of the second component along the length of the first component. The electronic-ink label device is connected to the variable resistor across the electrical contact, the moveable component of the drug delivery device comprises the first component or the second component, and the position of the second component with respect to the first component is changed during a dose setting operation or a dose dispending operation of the drug delivery device.

In some instances, the track comprises a single thread and the first and second conductors are disposed on opposite sides of a crest of the single thread, and wherein the second component is in threaded engagement with the first component.

In some instances, the track comprises a first thread and a second thread, and the first conductor is disposed along the first thread, and the second conductor is disposed along the second thread, and wherein the second component is in threaded engagement with the first component.

In some instances, the first component is a threaded sleeve configured to move helically with respect to the housing during a dose setting operation, and wherein the second component is a thread insert carried by the housing, wherein the moveable component is the threaded sleeve and the visual indication corresponds to a dose set during the dose setting operation.

In some instances, the first component is a leadscrew configured to move helically with respect to the housing during a dose dispensing operation of the drug delivery device to translate a stopper into a cartridge of the drug delivery device, wherein the second component comprises a bearing nut carried by the housing, and wherein the moveable component is the leadscrew and the visual indication corresponds to the position of the stopper in the cartridge.

In some instances, the first component is a threaded plunger rod, and the second component is a last dose nut configured to thread along the drive sleeve during the dose setting operation, and wherein the moveable component is the last does nut and the visual indication corresponds to a dose remaining in the drug delivery device.

In some instances, the wireless signal comprises identification information related to the drug delivery device or a medicament contained therein.

In some instances, the electronic-ink label includes an RFID device configured to transmit a wireless RFID signal representation of the visual indication to an external device.

In some instances, the electronic-ink label includes a battery for providing power to the printed electronics.

In some instances, the electronic-ink label includes an contact surface arranged to be adhered to the exterior of the housing.

In some instances, the electronic-ink label includes an outer surface comprising a display for showing the visual indication.

In some instances, the electronic-ink label includes an RFID module configured to transmit a wireless signal related to the position of the moveable component in response to the electrical property of the electric circuit.

DESCRIPTION OF FIGURES

FIG. 1B is a cross sectional view of a portion of the drug delivery device of FIG. 1A showing an electronic-ink label in electrical contact with an electric circuit of the drug delivery device.

FIGS. 2A and 2B are illustrations of a dose dispensing mechanism with a conductive track forming a variable electronic device of a dose tracking mechanism.

FIGS. 7A and 7B are illustrations of a dose memory mechanism with a conductive track forming a variable electronic device of a dose tracking mechanism.

DETAILED DESCRIPTION

Figure 1A:
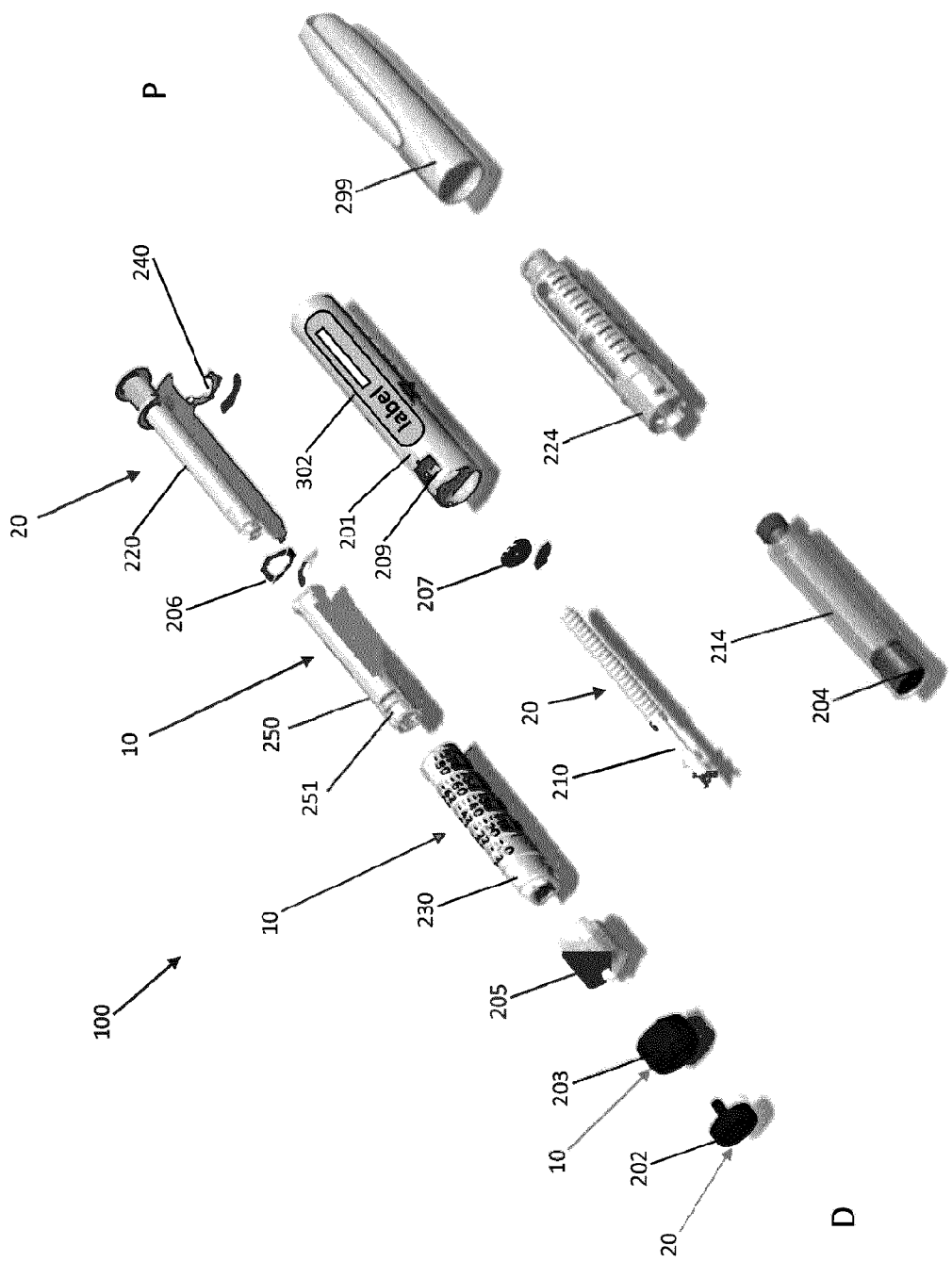
FIG. 1A is an exploded view of a drug delivery device with an electronic-ink label.

Cartridge-based injection and medical syringe systems can include integrated electronics that enable detection of a dose set by the user or a measurement of the medicament delivered by the device (e.g., a position sensor), along with some feature for presenting this information to the user. For example, a digital display arranged to display a dose or a wireless connection to transmit the dose data. However, the above examples typically require an internal source of power, either to run the sensor(s) or the wireless transmission. Certain aspects of the present disclosure provide an indication system including an electronic-ink label disposed on drug delivery device with a dose tracking mechanism or dose memory mechanism (e.g., a mechanism response to fill-level) generating a change in an electrical property of an electric circuit that is in electrical communication with the electronic-ink label on the drug delivery device. In some instances, the electronic-ink label includes a display (e.g., an electronic paper display) that provides a visual indication to a user regarding a status of the drug delivery device, such a current fill-level or an amount of a last dose dispensed from the device. In some instances, the electronic-ink label includes printed electronics and an internal source of power to provide electricity to the display. Certain aspects also relate to an electronic-ink label that generates a wireless RFID signal using an active (e.g., battery powered) or passive RFID transmitter.

Certain aspects of the present disclosure measure the amount of medicament dispensed from a container, e.g. a cartridge, and use this information to determine the amount of medicament that a patient has received during an injection event. The principle is based on attaching an electronic-ink label to the exterior of a drug delivery device that is able to sense the movement of components of the drug delivery device that are arranged to modify the electrical property of an electric circuit of the drug delivery device. The electric circuit includes electrical contacts on the exterior of the drug delivery device and the electronic-ink label is placed in contact with the electric contacts in order to be responsive to the changes in the electrical property of the electric circuit.

The electronic-ink label may include information related to, for example a unique tag serial number, or may be product-related information such as a stock number, lot or batch number, production date, or other specific information such as drug compound.

In an example embodiment, an electrical property (e.g., resistance) of an electric circuit in the drug delivery device is varied depending on the position of the last dose nut of a drug delivery device. For example, the thread on which it travels comprises a galvanic/conductive track that has a certain resistance. The resistance value varies with the position of the last dose nut. Adding this resistance to the electric circuit would result in a modified resistance that corresponds to the fill-level of the cartridge. The value of the resistance can be determined by electronic-ink label to displace a change in the visual indication. The amount of change in the resistance is proportional to the distance the last dose has traveled along the thread. As the resistance is varied with the position of the last dose nut, each position can be identified by electronic-ink label. In some instances, the electronic-ink label is calibrated during manufacturing or when the electronic-ink label, is initially attached the drug delivery device, when the resistance of the track is known to represent a full cartridge. In some instances, the resistance difference in relation to the initial resistance is taken as a measure and the difference is used to calculate an amount of medicament delivered or remaining.

In certain aspects, a variable electric component is provided as part of a dose tracking mechanism in a drug delivery device to modify the electrical property of an electric circuit in the drug delivery device in response to a movement of a dose tracking mechanism or a dose dispensing mechanism of the drug delivery device, such that an electronic-ink label is responsive to the electrical property and displays a visual indication that corresponds to the electrical property, where the visual indication is the dose set by the dose setting mechanism, the dose dispensed by the dose dispensing mechanism, the fill-level of the drug delivery device, or a status of one or more moveable components of the drug delivery device.

In a representative embodiment, an indication system includes an electronic-ink label and a drug delivery device with an electric circuit with a variable electronic device arranged to modify a property of the electric circuit (e.g., resistance, capacitance, inductance) in response to change in position of a component of the drug delivery device during a dose setting operation or a dose delivery operation, such that the variable electronic device changes an electrical property of the electric circuit. The electronic-ink label is configured to be disposed on the drug delivery device, where the electronic-ink label is in electrical contact with the electric circuit to measure the electrical property of the electric circuit and display an indication based on the electrical property.

In some instances, the variable electronic device is operatively connected to or integrated with a component of a dose setting mechanism, such that the indication of the electronic-ink label changes as a function of the dose set by the dose setting mechanism. In some instances, the variable electronic device is operatively connected to or integrated with a component of a dose dispensing mechanism, such that the electrical property of the electric circuit changes a function of the dose dispensed by the dose setting mechanism, which results in a corresponding change in the indication of the electronic-ink label. In some instances, the variable electronic device is operatively connected to or integrated with a component of a dose memory mechanism, such that the electrical property of the electric circuit changes as a function of the dose remaining in the drug delivery device which results in a corresponding change in the indication of the electronic-ink label.

In operation, the electronic-ink label is disposed on an exterior surface of a housing of the drug delivery device, and the electric circuit includes exterior contact points on the housing where the electronic-ink label can be in electrical communication with the electric circuit in order to be responsive to changes in an electrical property of the electric circuit. In some instances, the electric-ink label includes corresponding electrical contacts on the same side as the adhesive in order to interface with the electrical contacts of the drug delivery device when attached thereto. In this manner, for example, during a drug delivery operation, a dose dispensing mechanism moves an amount corresponding to the amount of medicament delivered. During this movement, the variable electronic device modifies a property of the electric circuit such that the indication of the electronic-ink label changes, and the change corresponds to the movement of the dose dispensing mechanism. In some instances, the electrical property of the electric circuit is measured by the electronic-ink label, and the amount of medicament delivered is determined based on a known relationship between the electrical property and the dispensed amount of medicament. The known relationship could be, for example, that a given resistance value corresponds to a specific dispensed amount. Alternatively, the relationship could be based on a comparison between a measuring of the electrical property prior to the dose dispensing operation, where a measured change corresponds to the dispensed amount. In other instances, it is not necessary to have a defined resistance (e.g. to display a certain fill level for a certain resistance value), instead it is sufficient to ensure that at the start, the display shows "full" and in the end the display shows "empty". Or the display could be segmented according to the amount of liquid in the medicament container. E.g., for a 3 ml cartridge containing 300 IU of Insulin it would be appropriate to have the display segmented in 300 elements. All elements are in the same status indicating "full" at the beginning. As the electrical property changes due to movement of a movable component the status of display elements change one after the other thus providing a fill level indication.

The processor in the electronic-ink label could also store how many display elements have undergone a status change at each instance thereby providing a dose history log. The dose history log could be transferred via RFID communication together with the other data.

In some instances, the electronic-ink label includes an active or an RFID system, which can be passive (i.e., no internal power source), or active, where active RFID chips are generally understood to require a source of power beyond any received RF energy in order to generate the wireless response signal with more power. The design is similar in function compared to the above passive system, with the addition of the electronic-ink label's battery being used to boost the transmission power of the RFID signal. The power is only required to feed the system when in use. In some examples, the electronic-ink label includes an air-zinc battery is used to ensure that the drug delivery device is disposable, if necessary. In some instances, the RFID device does not initially transmit the RFID signal until a user activates the drug delivery device (e.g., the electronic-ink label senses a change in the electrical property of the electric circuit) or until an external device queries the RFID device. In some instances, the actual data that is being sent from the RFID device in the wireless signal includes information on the medicament/device and this can be by the reader to interpret the data. For example, the external device can assign the measured frequencies to the "right" device and store it appropriately in a separate storage for this device/medicament.

FIG. 1A is an exploded view of a drug delivery device 100, which may be a disposable or reusable drug delivery device. The drug delivery device 100 includes a housing 201, covered by a replaceable cap 299, where the housing 201 contains a cartridge 214 and a cartridge housing 224 in which the cartridge 214 is disposed. An electronic-ink label 302 is shown attached to the housing 201, and discussed in more detail below. A stopper 204 is disposed in the body of the cartridge 214 and can be advanced within the cartridge 214 during use to expel medicament from the cartridge 214. A needle assembly can be affixed to the cartridge housing 224 or the cartridge 114 to deliver the medicament. To drive the stopper 204 into the cartridge 214, the drug delivery device 100 includes a plunger rod 210, a drive sleeve 220, and a trigger button 202 (e.g., a dose dispensing mechanism 20), which act together to drive a pressure plate 207 against the stopper 204 and into the cartridge 214. A medicament or drug dose to be ejected from the drug delivery device 100 is selected by turning a dosage knob 203, which is connected by a threaded insert 205 a dose dial sleeve 230, where rotation of the dose dial sleeve 230 by the dosage knob 203 causes the selected dose to be displayed in a dosage window 209 in the housing 201 and causes a clicker 250 to interact with the drive sleeve 220 via a spring clutch 206. Together, the dosage knob 203, dose dial sleeve 230, and clicker 250 are a dose setting mechanism 10. The dose dial sleeve 230 is arranged around a clicker 250, which includes a feedback mechanism 251 that generates a tactile or audible feedback with rotation of the dose dial sleeve 230. The clicker 250 is coupled to the drive sleeve 220 with a metal clutch spring 206, and a last dose nut 240 is provided on the drive sleeve 220. The last dose nut 240 advances with each dose dispensing operation to track the total medicament remaining in the cartridge 214. Finally, an injection button 202 is included, and depressing the injection button 202 activates a dose dispensing operation of the drug delivery device 100.

While the dose setting mechanism 10 is illustrated as the dosage knob 203, dose dial sleeve 230, and the clicker 250, as described above, one skilled in the art will appreciate that any number of different dose setting mechanisms are routine in the art for the purposes of setting a dose of a drug delivery device and aspects of the present disclosure are compatible with other such dose setting mechanisms. Similarly, while the dose dispensing mechanism 20 is illustrated as including the plunger rod 210, drive sleeve 220, trigger button 202, one skilled in the art will appreciate that any number of different dose dispensing mechanisms (e.g., drive mechanisms) are routine in the art for the purposes of delivering or dispensing a dose of a drug delivery device and aspects of the present disclosure are compatible with other such dose dispensing mechanisms.

Continuing with the operation of the drug delivery device 100, turning the dosage knob 203 causes a mechanical click sound to provide acoustical feedback to a user by rotating the dose dial sleeve 230 with respect to the clicker 250. In some instances, numbers displayed in the dosage display 209 are printed on the dose dial sleeve 230 that is contained in the housing 201 and mechanically interacts with the drive sleeve 220 via the metal spring clutch 206 to interact with the cartridge 114. When the injection button 202 is pushed, the drug dose displayed in the dosage window 209 will be ejected from the drug delivery device 100. During a dose setting operation, the drive sleeve is helically rotated with the dose dial sleeve 230 in the distal direction D. When the injection button 202 is pushed, the drive sleeve 220 is released and advanced proximally, which causes rotation of the plunger rod 210. The rotation of the plunger rod 210 drives the pressure plate 207 against the stopper 204 of the cartridge 214, which drives the stopper 204 into the cartridge 214 to expel the medicament from the cartridge 214. A more detailed description of a representative drug delivery device is described in U.S. Pat. No. 7,935,088 B2, issued May 3, 2011, which is incorporated herein by reference.

FIG. 1B is a cross sectional view of a portion of the drug delivery device 100 of FIG. 1A. FIG. 1B shows the drug delivery device 100 at the end of a dose setting operation and prior to a dose dispensing operation, where the dose dial sleeve 230 and the drive sleeve 220 have been helically rotated with respect to the housing 201 and a threaded end 215 of the plunger rod 210 to set the dose. The last dose nut 240 is shown advanced along the drive sleeve 220 from an initial position to a position indicative of the dose remaining in the drug delivery device 100. Upon activation of the injection button 202, the drive sleeve 220 advances into the housing 201 and a bearing nut 208 induces rotation of the plunger rod 210. The bearing nut 208 sits fixed inside the housing 201 and has a threaded engagement with a plunger rod 210. As the piston rod 210 rotates, the plunger rod 210 is screwed forward (relative to the housing 201) because the bearing nut 208 cannot move. The rotation of the piston rod 210 drives the plunger rod 210 and the pressure plate 207 proximally to drive the stopper 204 into the cartridge 214 (FIG. 1A).

FIG. 1A also shown the electronic-ink label 302 disposed around an external portion of the housing 201. The electronic-ink label 302 includes printed electronics 320 that are in electrical communication with an electric circuit inside the drug delivery device 100. The external surface of the housing 201 includes electric contacts 308 that provide the electronic-ink label 302 a point of electrical communication with the electric circuit inside the drug delivery device 100. In some instances, the electric circuit is formed as part of moveable components of the drug delivery device 100, such as the dose dispensing or setting mechanisms 10, 20 or the last dose nut 240, such that an electrical property of the electric circuit is modified by the current configuration or position of the moveable components and the electronic-ink label 302 is able to measure the electrical property (or otherwise be responsive to it), in order to display an indication of the configuration or position of the moveable components. In some instances, the electronic-ink label 302 is in electric communication with the last dose nut 240 and the electronic-ink label 302 includes a display showing a visual indication of the fill level of a cartridge of the drug delivery device 100, which is a function of the position of the last dose nut 240. In some instances, and as explained in more detail below with respect to FIG. 2A, the electric contacts 308 are connected to the electric circuit via electric brushes 218a, 218b that travel along conductive tracts of a moveable component of the drug delivery device 100.

FIGS. 2A and 2B are illustrations of a dose dispensing mechanism with an electric circuit constructed from conductive elements 212a, 212b in individual grooves 211, 213, which together create a variable electronic resistor for use as a dose tracking mechanism. One aspect of the present disclosure is based on modulating an electric property (e.g., resistance) of an electric circuit as a function of the position of the plunger rod 210 (e.g., a leadscrew), which is a key component of the dose dispensing mechanism 20 of the drug delivery device 100 for use in expelling a dose of medicament. In dispensing a dose, the position of the plunger rod 210 changes with respect to the bearing nut 208 by rotating with respect to the bearing nut 208, and thus moving proximally along the axis of rotation. FIG. 2A shows a plunger rod 210 with embedded conductive elements 212a, 212b and stationary brushes 218a, 218b (e.g., conductive brushes, or electric brushes) forming a variable resistor that changes the resistance across the stationary brushes 218a, 218b as they move along the embedded conductive elements 212a, 212b. The plunger rod 210 thread has two parallel oriented grooves 211, 213 that include one of the embedded conductive elements 212a, 212b along the length of each the two parallel oriented grooves 211, 213 without interfering each other, except at one end of the grooves 211, 213 to create an open circuit across the brushes 218a, 218b.

In operation, the plunger rod 210 is driven proximally by the drive sleeve 220, and the grooves 211, 213 are threaded through the bearing nut 208, such that the proximal movement of the plunger rod 210 generates rotates the plunger rod 210 as it passes through the bearing nut 208. The stationary brushes 218a, 218b are disposed on the bearing nut 208 or otherwise fixed to the housing 201 and the electronic-ink label 302 is connected across the brushes 218a, 218b via the electric contacts 308 on the external surface of the housing 201. The resistance across the brushes 218a, 218b, and therefore the electric contacts 308, changes because of the change in total length of the conductive elements 212a, 212b between the brushes 218a, 218b. For example, as shown in FIG. 2A (and in FIG. 1B), the stationary brushes 218a, 218b contact the conductive elements 212a, 212b close to the proximal end of the grooves 211, 213. The conductive elements 212a, 212b are in contact at either the proximal end or distal end of the grooves 211, 213, but not both. If at the distal end, the electric path from one brush 218a to the other brush 218b is down the entire length of the first groove 211 and back down the entire length of the second groove 213, a condition representing the highest resistance configuration of the system. As the plunger rod 210 is driven though the bearing nut 208, the brushes 218a, 218b move along the grooves 211, 213, and the resistance between the brushes 218a, 218b decreases as the total length of the conductive elements 212a, 212b between the brushes 218a, 218b decreases. Alternatively, if the conductive elements 212a, 212b are in electrical contact at the proximal end, then the opposite configuration is true, and the resistance across the brushes 218a, 218b is at a minimum as shown, and increases at the plunger rod 210 is driven though the bearing nut 208. In some instances, each specific resistance represents one position of the plunger rod 210 and therefore the resistance corresponds to an amount of the dose expelled from the cartridge 214 by the plunger rod 210. In other instances, a change in the resistance corresponds to a change in position and is therefore proportional to the amount of medicament. Therefore, a relative change in resistance as compared to an initial resistance (e.g., before injection, or before a first use) corresponds to a measure for the medicament amount that has been expelled. As explained in more detail below with regard to FIGS. 3A-C, the electronic-ink label 302 is connected across the brushes 218a, 218b such that the change in resistance can be sensed by the electronic-ink label 302 and used to change a visual indication of the electronic-ink label 302.

FIG. 2B is a schematic of an alternative configuration, where electronic-ink label 302 is connected across the closed end of the conductive elements 212a, 212b, and a brush 282 completes the circuit across the conductive elements 212a, 212b at a variable location along the grooves 211, 213.

Figure 3A:
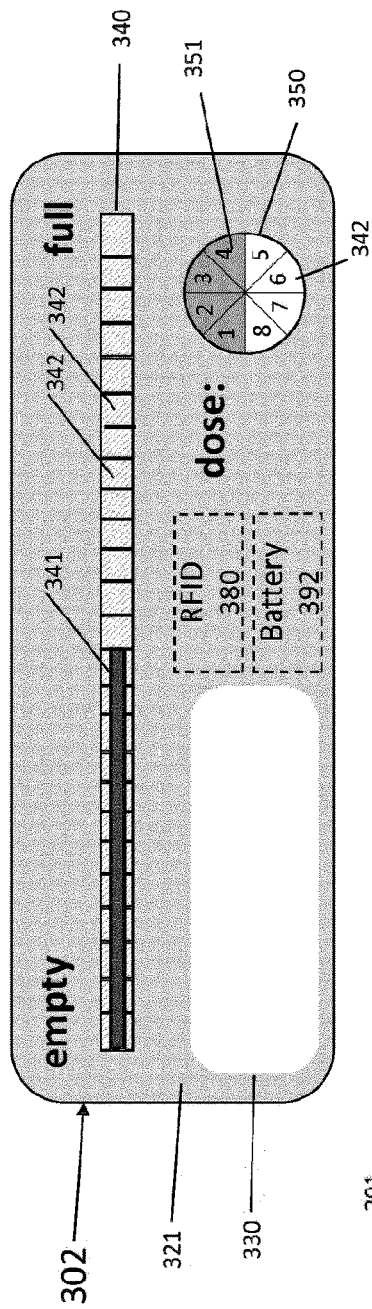
FIG. 3A is an illustration of an electronic-ink label.

FIG. 3A is an illustration of an electronic-ink label 302, which may be, e.g., a thin film smart label including printed electrics. The electronic-ink label 302 includes an outer surface 321 with an informational label 330 displaying product and medicament information to the user for use in identifying and operating the drug delivery device 100. The outer surface 321 also includes a fill-level display 340 configured to display a fill-level indication 341. In some instances, the fill-level display 341 comprises a plurality of display elements 342, and the fill-level indication 341 represents the display elements that have switched from an 'off' state or an 'on' state. The fill-level display 340 is part of, or controlled by, printed electrics that are integrated into the electronic-ink label 302. In operation, the printed electrics are in electrical communication with the electric circuit of the drug delivery device 100 when the electronic-ink label 302 is disposed on the exterior surface of the housing of the drug delivery device 100, and the fill-level display 340 of the electronic-ink label 302 changes the fill-level indication 351 in response to changes in the electrical property of the circuit. In some instances, there is a direct connection between the display of the e-ink label and circuitry of the drug delivery device, with no data processor required to calculate a dose size from an electrical property and generate instructions to drive a display. In some instances, the fill-level display 340 is an Electronic Paper Display (EPD) or similar low-power reflective-light display technology. The electronic-ink label 302 also includes a power source, such as a battery 392, integrated into the electronic-ink label 302 in order to power the printed electrics 320 and the fill-level display 340. In some instances, the electronic-ink label 302 includes additional displays, such as a dosage display 350 configured to display a dosage indication 351 in response to a set or dispensed dose. For example, the dosage display 350 be responsive to an electric circuit in a dose setting mechanism 10 to display the set dosage to a user prior to a dose dispensing operation, or, alternative, the dosage display 350 is response to an electric circuit in a dose dispensing mechanism 20 to display the amount of medicament dispensed after a dose dispensing mechanism. In some instances, the dosage display 350 is configured to show an indication 351 to the user of the dose last set or delivered by the drug delivery device 100 in order to remind the user. In some instances, the electronic-ink label 302 includes an RFID chip 380 which includes an antenna to transmit a wireless signal to an external device, where the wireless signal includes information regarding the indications (e.g., the fill-level indication 341 and the dosage indication 351). In some instances, the wireless signal includes information similar to that shown on the information label 350, for example, drug type/name, concentration, fill date, lot no, expiry date, etc. The RFID device 380 could be a passive device or an active device, and operate using a frequency-modulation means, as described in more detail in EP Patent Application EP17306864.4, Filed Dec. 21, 2017.

Figure 3B:
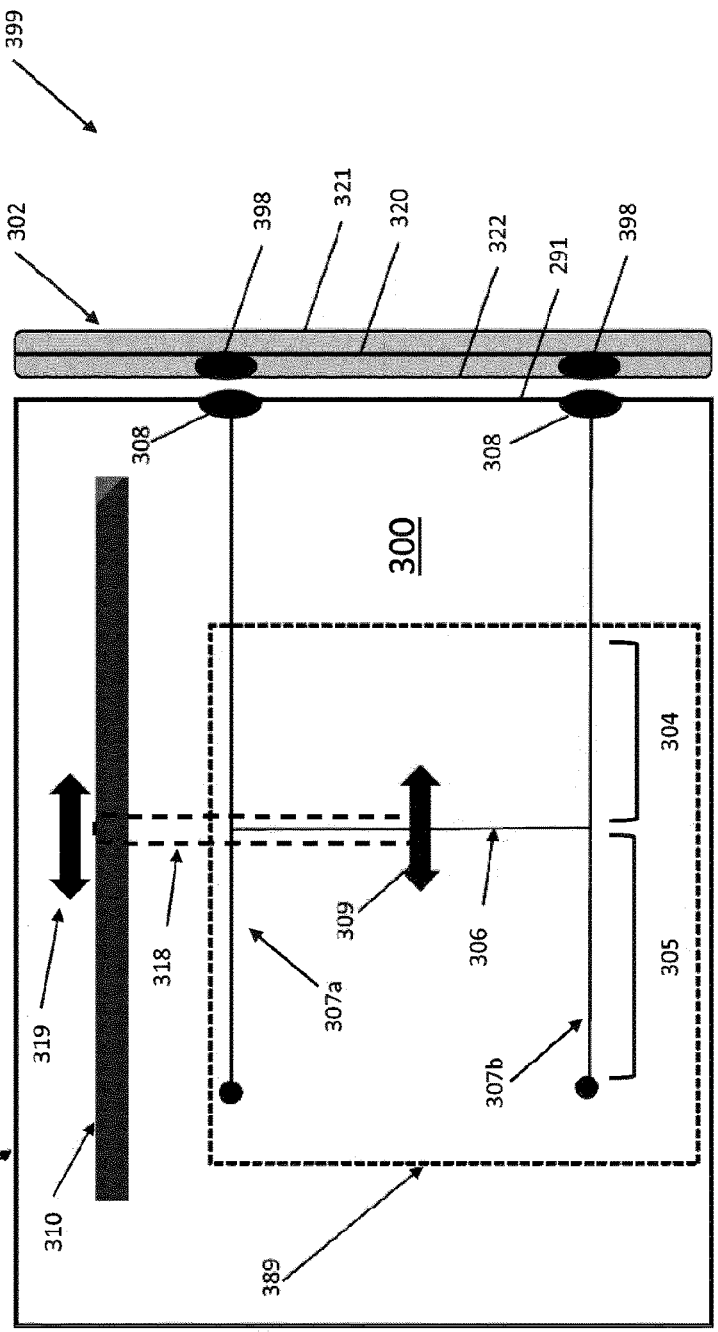
FIG. 3B is an illustration of a dose tracking mechanism in electrical communication with an electronic-ink label.
Figure 3C:
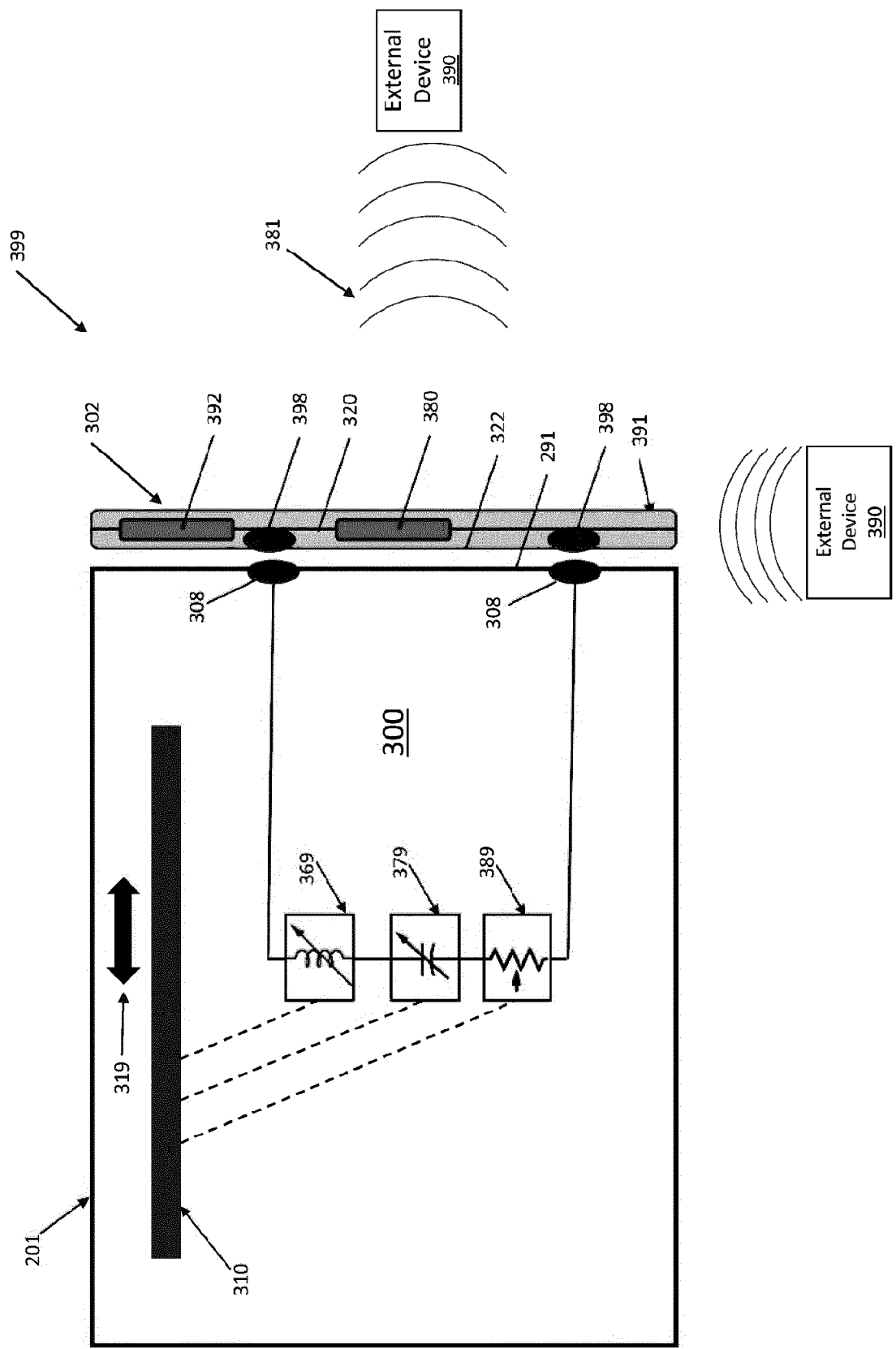
FIG. 3C is an illustration of an electronic-ink label with an integrated RFID device

FIGS. 3B and 3C are illustrations of an indication system 399 including electronic-ink label 302 and an electric circuit of the drug delivery device 100. FIG. 3B is a schematic of the operation electronic-ink label 302 connected to the electric circuit 300 of the drug delivery device 100, where the electric circuit 300 includes a variable resistor 389 arranged to modify resistance of the electric circuit 300 in response to the position of a moveable component 310 of the drug delivery device 100. The variable resistor 389 is operatively coupled to the moveable component 310 of the drug delivery device 100, such that movement of the component 310 (indicated by an arrow 319) results in a corresponding change in the resistance of the variable resistor 389, as detailed below. As detailed below, the variable resistor 389 changes the overall resistance of the electric circuit 300, which enables the electronic-ink label 302 to change the indication 341 as a function of the actuation of the variable resistor 389 during operation of the drug delivery device 100. For example, the modulation can be a change in the resistance of the electric circuit 300, which is an easily detectable property of the electric circuit 300 by the electronic-ink label 302 when it is in direct contact with the electric circuit 300 via the electrical contacts 308 on the exterior surface 291 of the housing 201 of the drug delivery device 100. FIB. 3B shows the electronic-ink label 302 with corresponding electrical contacts 398 on an inner surface 322 that are arranged to directly contact the electrical contacts 308 of the housing 201. In some instances, the electrical contacts 398 are sufficiently large to enable reliable electrical connection between the electric circuit 300 of the drug delivery device and the electronic-ink label 302. For example, the contacts 398 being at least twice the size as the corresponding contacts 308 would provide reliable electrical connection even if the label is not exactly positioned on the drug delivery device, thereby compensating for any variation in the positioning of the label during assembly of the device.

In operation, the moveable component 310 of the drug delivery device 100 is configured to operate the electric component 318 of the variable resistor 389 during a dose setting operation or a dose dispensing operation. For example, FIG. 3B shows that the variable resistor 389 includes two elongated conductive elements 307a, 307b, similar to the conductive elements 212a, 212b of FIG. 2A. Also similar to the brushes 218a, 218b of FIG. 2, in FIG. 3B a moveable electric connection 306 spans between the elongated conductive element 307a, 307b and puts them in electrical contact with each other. The elongated conductive elements 307a, 307b are connected at one end to the rest of the electric circuit 300 and the location of the moveable electric connection 306 along the elongated conductive elements 307a, 307b determines the overall resistance of the electric circuit 300 (e.g., by determining the overall portion of the elongated conductive element 307a, 307b that are in an electric circuit with the electric connection 306). The moveable electric connection 306 is connected to the moveable component 310 of the drug delivery device 100 via the electric component 318, which could be, for example, a nut having electric brushes (e.g., the moveable electric connection 306) in contact with elongated conductive elements 307a, 307b. As illustrated, the location of the moveable electric connection 306 along the elongated conductive elements 307a, 307b results in a first portion 304 of the elongated conductive elements 307a, 307b to be in the electric circuit 300, and a second portion 305 of the elongated conductive elements 307a, 307b to be outside of the electric circuit 300. Movement of the electric connection 306 along the elongated conductive elements 307a, 307b changes the length of the first and second portions 304, 305, and thereby varies the resistant of the variable resistor 389 of the electric circuit 300.

One skilled in the art will appreciate that the configuration of FIG. 3B (with a stationary track and moveable electric connection 306) is the inverse of FIG. 2, where the conductive elements 212a, 212b move and the brushes 218a, 218b are stationary), but the variable resistant result of both configurations (FIG. 3B and FIG. 2) is the same.

In some instances, the moveable component 310 is part of a dose setting mechanism 10 such that moveable component 310 is moved during a dose setting operation, which results in a movement of the electric component 318 and, therefore, a change in the resistance of the variable resistor 389 corresponds to the movement of the dose setting mechanism and an amount of the dose set by the dose setting mechanism. In some instances, the moveable component 310 is part of a dose dispensing mechanism 20 such that moveable component 310 is moved during a dose dispending operation, which results in a movement of the electric component 318 and, therefore, a change in the resistance of the variable resistor 389 corresponds to the movement of the dose dispensing mechanism and an amount of the dose dispensed by the dose dispensing mechanism. In both cases, movement of the dose dispensing mechanism 20, dose setting mechanism 10, or some other mechanism of the drug delivery device (e.g., a dose memory mechanism) causes the electric component 318 to change the position of the electric connection 306 of the variable resistance 389, and thereby change the electrical property of the electric circuit 300 such that the display 350 of the electronic-ink label 302 shows an indication 351 of the position of the mechanism that is operatively coupled to the dose tracking mechanism 20. In addition, the movement of the component 310 that is actuated during operation of the drug delivery device 100 (e.g., the dose setting and/or the dispensing action) may involve rotational movement, as shown in FIG. 2B; alternatively, linear movement of the component 310 may also be used to operate the variable resistor 389, as shown in FIG. 3B.

Any number of variable electric components (of which a variable resistor 389 is one example) registers operation of some mechanism of the drug delivery device 100 (e.g., during a dial and/or dispense operation) and correlates this to modulate the electrical property of the electric circuit 300. FIG. 3C illustrates different variable electric components 369, 379, 389 arranged in the electric circuit 300. In some instances, the variable electric component is a variable inductor 369, and, in other instances, the variable electric component is a variable capacitor 379. One or more of the variable electric components 369, 379, 389 could be used in the indication system 399 to modulate the electrical property of the electric circuit 300. For example, the modulation can be a change in the resistance of the electric circuit 300, which is an easily detectable property of the electric circuit 300 by the electronic-ink label 302 when it is in direct contact with the electric circuit 300 via the electrical contacts 308 on the exterior surface of the housing 201 of the drug delivery device 100. The variable electric components 369, 379, 389 can be arranged to modify the electrical property of the electric circuit 300 in almost any matter that corresponds a movement of the mechanism of the drug delivery device 100 to which the variable electric components 369, 379, 389 is operatively coupled. In some instances, a variable electric component 369, 379, 389 is operatively coupled to a dose dispensing mechanism 20, and the value of the electrical property of the electric circuit 300 is proportional to the position of the plunger rod 210 after a dose dispensing operation. In this example, the value of the electrical property of the electric circuit 300 is an indication of the amount of dose dispensed from the drug delivery device 100. In another example, the electrical property is correlated to the dose that has been dialed or set. However, such an example, the drug delivery device may include a mechanism that can distinguish between up and down dialing and should "know" when a setting operation is ended (e.g., by sensing the start of the dose dispensing operation).

In an alternative dose tracking mechanism configuration, a variable electric component 369, 379, 389 is arranged to be contacted or operated by contact with any adjacent components of the drug delivery device 100 that move relative to one another during operation (dose setting and/or dose dispensing). For example, movement between the dosage knob 203 and housing 201, between the dose dial sleeve 230 and the dosage window 209, or between the dose dial sleeve 230 and the housing 201.

FIG. 3C also shows a cross-section of the electronic-ink label 302, showing the battery 392 configured to provide power to the displays 340, 350 and the RFID device 380. However, as described above, the RFID device 380 can also be a passive RFID system, and FIG. 3C shows an external device 390 providing a wireless reader signal 391 to the antenna 301 of the RFID device 380 in order to generate power for the RFID chip 380. When powered (e.g., by the RF energy from the wireless reader signal 391), an antenna of the RFID device 380 transmits a RFID signal 381 at a resonance frequency of the RFID device 380. The RFID signal 381 can then be received by the external device 390. In some instances, the resonance frequency of the RFID signal 381 can be modulated by the RFID device 380 to encode the indication sensed by the electronic-ink label 302. For example, as detailed above, the variable resistor 389 changes the overall resistance of the electric circuit 300, which enables the RFID device 380 to transmit the RFID signal 381 at variable frequency, depending on the actuation of the variable resistor 389 during operation of the drug delivery device 100. In other instances, the RFID device 380 encodes indication into the RFID signal 381.

In some instances, the electric circuit 200 the RFID device 380 are electrically connected via the printed electronics 320 of the electronic-ink label 302. The RFID device 380 could be on the exterior of the electronic-ink label 302, preferably as a label (plastic, paper, adhesive RFID chip) in contact with the printed electronics 320. Alternatively, the RFID device 380 could be integrated with the electronic-ink label 302, either as part of the printed electronics 320 or as a separate module in the construction of the electronic-ink label 302.

Figure 4:
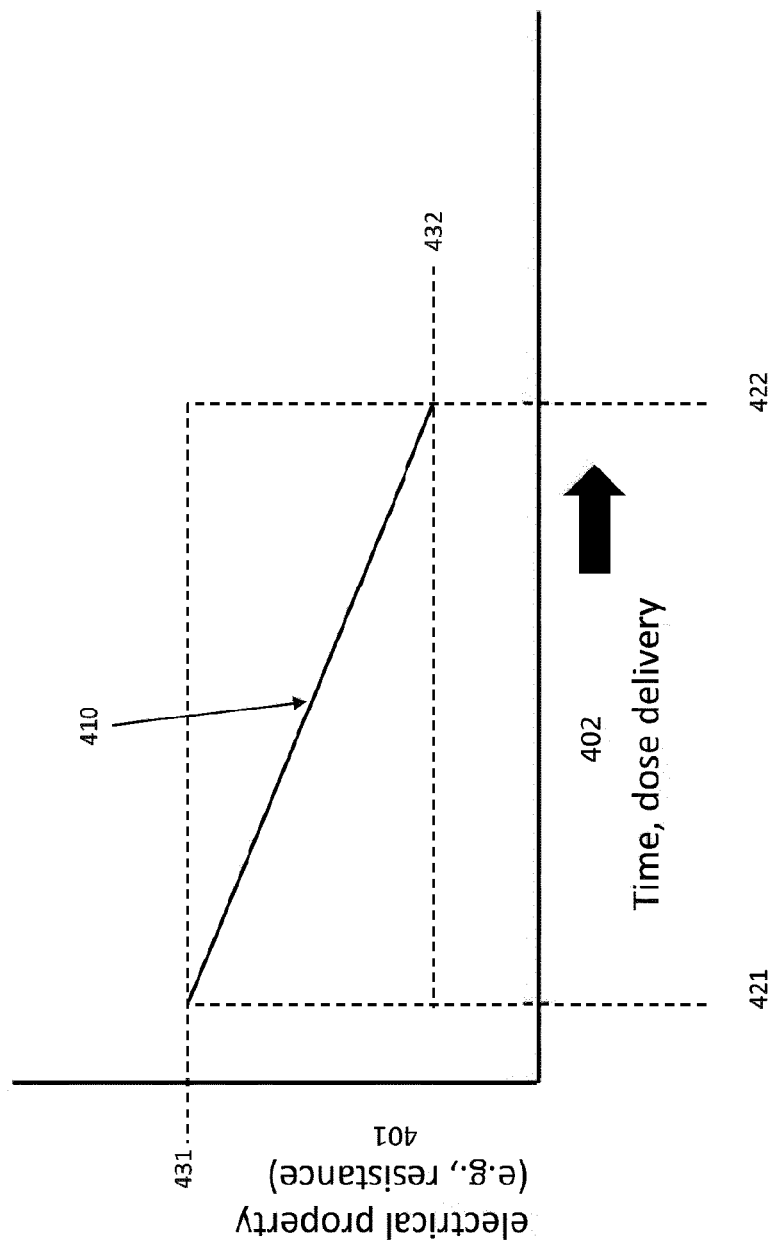
FIG. 4 is a graph of a change in the value of an electrical property of the electric circuit coupled to a dose dispensing mechanism during a dose dispensing operation.

FIG. 4 is a graph of resonance electrical property (e.g., resistance) 401 vs. time 402, and shows a change in the electrical property 410 of the electric circuit 300 coupled to a dose dispensing mechanism 20 during a dose dispensing operation. FIG. 4 illustrates how the electrical property 410 sensed by the electronic-ink label 302 changes during a dose dispensing operation, where a variable electric component 369, 379, 389 of the electric circuit 300 is operatively coupled with an element of the dose dispensing mechanism 20 and connected to the electronic-ink label 302 on the exterior of the housing 201. For example, a variable resistor 389 is arranged in the plunger rod 210 of a drug delivery device (e.g., FIG. 2B), such that the resistance of the variable resistor 389 increases as the plunger rod 210 is advanced during the dose dispensing operation from a first location at time 421, to a second location, at time 422. This change in position of the plunger rod 210 causes the variable resistor 389 to, for example, increase the total resistance of the electric circuit 300, which results in a decrease in the electrical property 410 as sensed by the electronic-ink label 302.

FIG. 4 illustrates how the value of the electrical property 410 of the electric circuit 300 decreases from a first value 431 at the first time 421 (e.g., before or at the start of the dose dispensing operation) to a second value 432 at the second time 422 (e.g., after or at the end of the dose dispensing operation). In some instances, the second value 432 corresponds to the amount of the dose dispensed from the drug delivery device 100, where the first value 431 represents the resistance of the electrical circuit prior to the drug delivery operation, and the second value 432 represents the resistance afterwards due, for example, the change in the position of a component of the drive mechanism. In some instances, the drug delivery device is capable of multiple drug delivery operations, in which case FIG. 4 is illustrative of the resistance change occurring during each drug delivery operation, where the second value 432 of a first operation represents the first value 431 of an immediately subsequent drug delivery operation. In some instances, the value of the difference between the first value 431 and the second value 432 corresponds to the amount of the dose dispensed from the drug delivery device 100. Generally, the electronic-ink label 302 need not measure the entire history of the electrical property 410 across the dose dispensing operation, but only measure the value at either the second time 422 or at the first and second times 421, 422, as detailed above. While FIG. 4 illustrates the change in electrical property 410 with respect to time 402 as linear during a dose dispensing operation, other relationships are possible, if not more likely due to the typical non-constant movement of a plunger rod 210 during a dose dispensing operation. In many instances, the shape of the curve of the electrical property 410 does not matter, as any measured value of the electrical property can, some instances, correspond directly a position 319 of the plunger rod 210 (e.g., an amount of medicament dispensed), and there need not be a 1:1 correspondence such that an equal change in electrical property 410 corresponds to an equal change in position 319. In still other instances, and in the case of an auto-injector where the force delivery of the dose dispensing mechanism is known, the electronic-ink label can measure the shape of the curve of the electrical property 410 during the dose dispensing operation, where the shape can indicate other properties of the dose dispensing operation. Such as, for example, the rate of injection, which can be further used to calculate properties of the drug delivery device (e.g., restriction in the medicament flow, or a defect in the dose dispensing mechanism 20), properties of the medicament (e.g., viscosity and/or temperature), or properties of the patient's injection site.

Figure 5A:
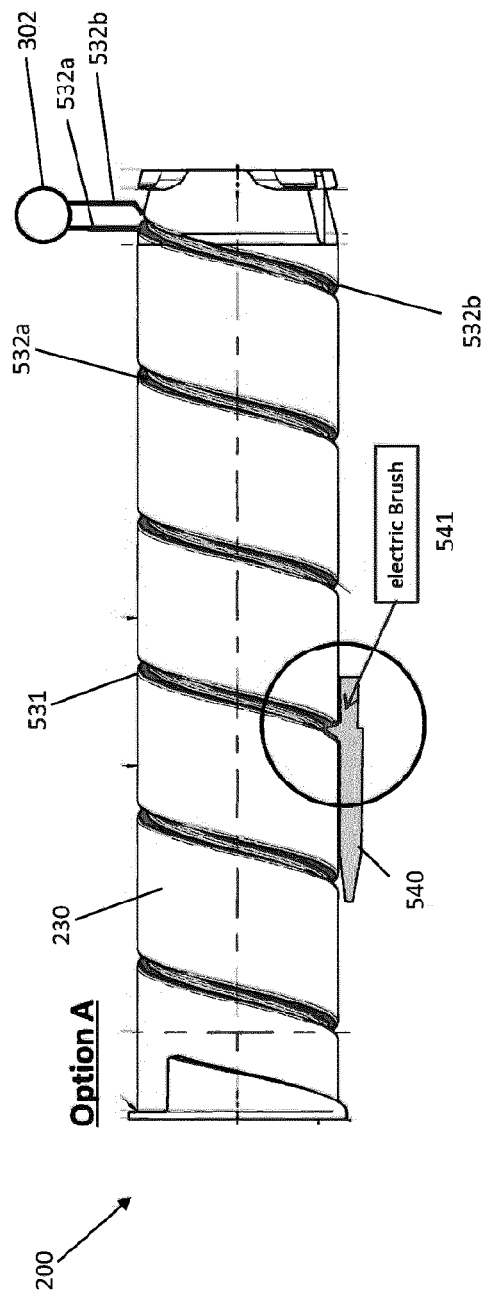
FIGS. 5A and 5B are illustrations of a dose setting mechanism with a conductive track forming a variable electronic device.
Figure 5B:
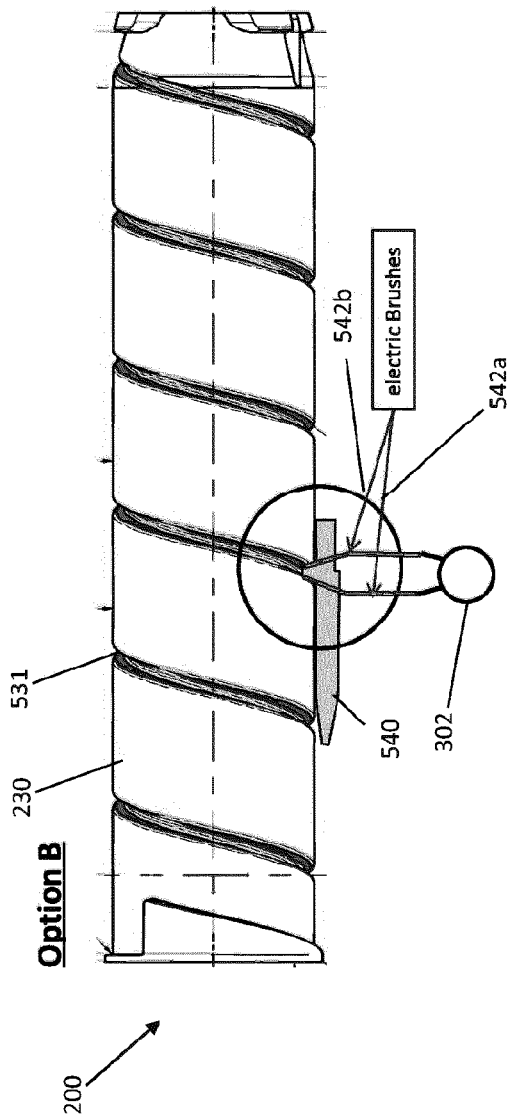

FIGS. 5A and 5B are illustrations of a dose setting mechanism with a conductive track forming a variable electronic device of a dose tracking mechanism. FIG. 5A shows a dose dial sleeve 230 (e.g., a number sleeve) with a single groove 531 arranged helically around the exterior of the dose dial sleeve 230. The track 531 includes first and second conductive elements 532a, 532b embedded along the grove 531 without interfering each other. The conductive elements 532a, 532b have a specific resistance, which behaves proportionally to the length.

In FIG. 5A, a thread insert 540 is shown integrated on the inside of the housing 201 (FIG. 1). The thread insert 540 includes an electric brush 541 traveling along the track 531 and in contact with both of the first and second conductive elements 532a, 532b to create a closed end of a circuit. The other end of the circuit is completed with an electronic-ink label 302 in contact across the first and second conductive elements 532a, 532b. Together, the first and second conductive elements 532a, 532b and the electric brush 541 define a variable resistor 389 in the electric circuit 300, as described above. In operation, rotational movement of the dose dial sleeve 230 advances the or retracts the dose dial sleeve 230 from the housing 201, which also results in the thread insert 540 traveling along the track 531 at a location corresponding to the position of the dose dial sleeve 230. When a user of the drug delivery device commences a dose setting operation to a dose, the position of the dose dial sleeve 230 changes through its thread by rotating, and thus moving proximally along the rotating axis with respect to the housing 201. This proximal move also translates the trigger button 202 disposed at the distal end of the dose dial sleeve 230. To dispense the pre-dialed dose, the trigger button 202 is pressed and the dose dial sleeve 230 is driven into the housing 201 by the user until the dose dial sleeve 230 returns to a zero dose (e.g., initial) position. In this manner, position of the brushes 541 in the track 531 at the end of the dose setting operation indicate the amount of dose set by the user to be subsequently injected.

FIG. 5B shows an alternative configuration of the dose dial sleeve of FIG. 5A, where the electric circuit includes conductive elements on the thread insert 540. In FIG. 5B, the first and second conductive elements 532a, 532b are connected at one end of the track 531 and first and second brushes 542a, 542b in the thread insert 540 individual contact the first and second conductive elements 532a, 532b and the electronic-ink label 302 is connected across the first and second brushes 542a, 542b.

In some instances, the thread insert 540 is an external component of drug delivery device 100 an the electronic-ink label 302 is on the exterior of the thread insert 540 and connected across the first and second brushes 542a, 542b, which are exposed to the exterior surface.

Figure 6:
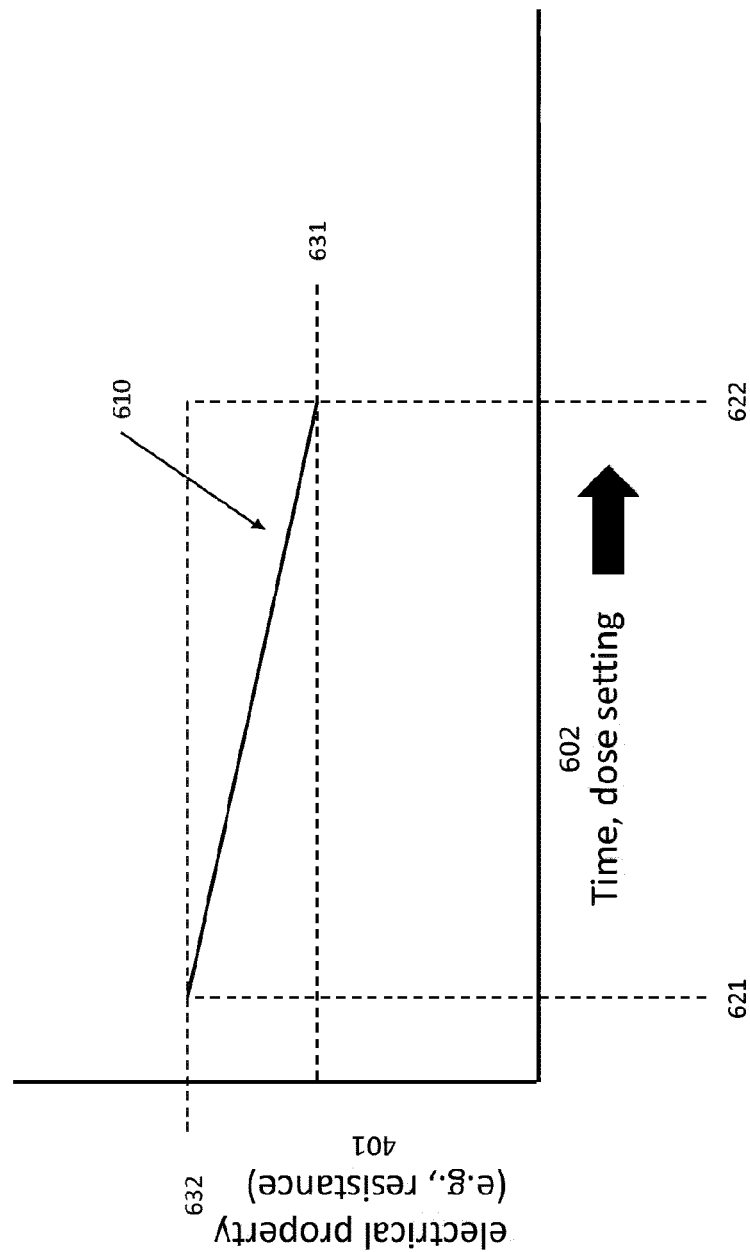
FIG. 6 is a graph of a change in the value of an electrical property of the electric circuit coupled to a dose setting mechanism a dose setting operation.

FIG. 6 is a graph of a change in the value of an electrical property of an electric circuit coupled to a dose setting mechanism of during a dose setting operation. FIG. 6 illustrates how the electrical property 610 of the electric circuit 300 decreases from a first value 631 at the first time 621 (e.g., before or at the start of the dose setting operation) to a second value 632 at the second time 622 (e.g., after or at the end of the dose setting operation). In some instances, the second value 631 corresponds to the amount of the dose set by the drug delivery device 100. In some instances, the value of the difference between the first value 631 and the second value corresponds to the amount of the dose set by the dose setting mechanism of the drug delivery device 100. Generally, the electronic-ink label 302 need not measure the entire history of the electrical property 610 across the dose setting operation, but only measure the value at either the second time 622 or at the first and second times 621, 622, as detailed above. While FIG. 6 illustrates the change in electrical property 610 with respect to time 602 as linear during a dose setting operation, other relationships are possible, if not more likely due to the typical non-constant movement of the dose dial sleeve 230 during a dose setting operation. In many instances, the shape of the curve of the electrical property 610 does not matter, as any measured value of the electrical property can, some instances, correspond directly a position 319 of the dose dial sleeve 230 (e.g., an amount of medicament set by the user), and there need not be a 1:1 correspondence such that an equal change in electrical property 610 corresponds to an equal change in position 319.

Figure 7B:
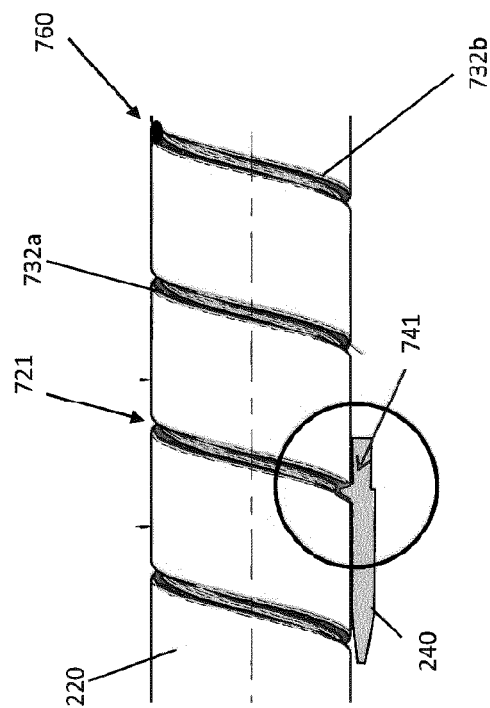

FIG. 7A is an illustration of a dose memory mechanism including a last dose nut 240 traveling along a conductive track 721 of the drive sleeve 220, which together form a variable electronic component of an electric circuit 300. FIG. 7B shows the conductive track 721 includes parallel conductive elements 732a, 732b that sit on each side of the tread in the drive sleeve 220 and is closed by a bridge 760 at one end. The last dose nut 240 includes part of the electric circuit 300 with two contacts 741 that each connect to one of the two conductive elements in the conductive track 721, thereby putting the conductive track 721 in the electric circuit 300 with the last dose nut 240. The length of the conductive track 721 that is included in the electric circuit 300 varies with the position of the last dose nut 240, and the position of the last dose nut 240 varies in the same way that the resistance changes in the electric circuit 300. In operation, the last dose nut 240 is advanced along the conductive track 721 during a dose dispensing operation to a position proportional to the dose of medicament remaining in the drug delivery device 100, where a value of the electric circuit 300 is a function of the position of the last dose nut 240 and an attached electronic-ink label 302 is in electrical communication with the electric circuit 300 to display an indication 341 corresponding to the position of the last dose nut 240.

Figure 8:
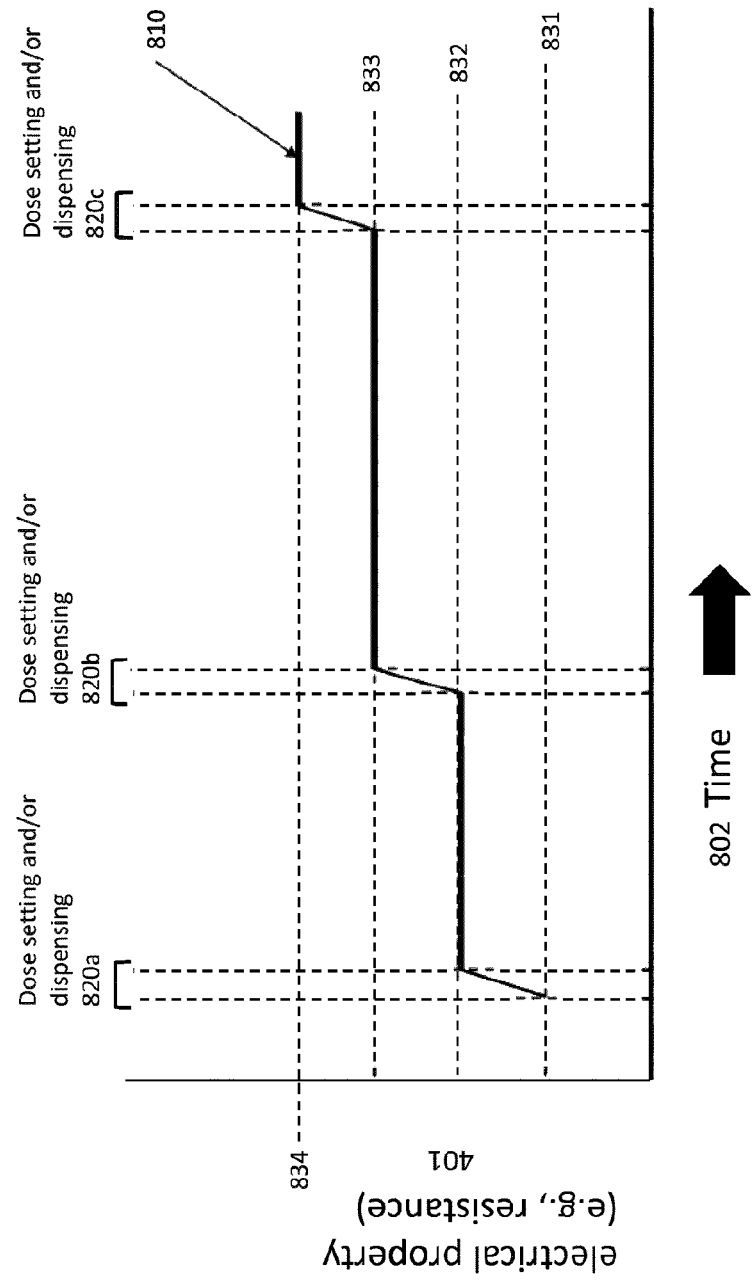
FIG. 8 is a graph of a change in the value of an electrical property of the electric circuit coupled to a dose memory mechanism during multiple dose dispensing operations.

FIG. 8 is a graph of a change in an electrical property of an electric circuit 300 coupled to a dose memory mechanism during multiple dose dispensing operations. FIG. 8 illustrates how the electrical property 810 of the electric circuit 300 increases from an initial value 831 to a first value 832 during a first dose dispensing operation 820a, and then to a second value 833 during a second dose dispensing operation 820b, and finally to a third value 834 during a third dose dispensing operation. In some instances, the initial value 831 corresponds to the position of the last dose nut 240 in the drug delivery device 100 before any use (e.g., as packaged during manufacture). This initial position of the last dose nut 240 corresponds to an initial amount of the medicament in the drug delivery device 100, therefore, the value of the first value 832 corresponds to an amount of medicament remaining in the drug delivery device 100 after a first dose dispensing operation 820. Similarly, the second and third values 833, 834 correspond to an amount of medicament remaining in the drug delivery device 100 after second and third dose dispensing operations 820b, 820c, respectively. Generally, the external device 390 need not measure the entire history of the electrical property 810 across the dose dispensing operations, but only measure the electrical property at either some time before or after each dose dispensing operation 820a-c, as detailed above.

Aspects of the systems disclosed above enable medical injectors to employ 'smart' technologies by way of an attached electronic-ink label in electrical communication with an electric circuit in certain moveable components (e.g. dose tracking mechanism, last dose nut) to give a certain features to a drug delivery device (e.g. of a pen-type injector). When integrating electronics into drug delivery device, a one or more components may be active (e.g., a sensor to measure certain properties of the injector or cartridge) and require an energy source, which typically could be a battery. One alternative is to use a means of energy harvesting as a power source replacement for a battery.

While the above descriptions refer to two conductive elements spanning a single track (e.g., track 531 of FIG. 5A) or two conductive elements spanning individual tracks (e.g., grooves 211, 213 of FIG. 2A), one skilled in the art will appreciate that single track configurations other configurations are suitable for constructing a variable electronics device. For example, in FIG. 7, the conductive track 721 may include a single conductive element, which is contacted by the last dose nut 240. In a single-track embodiment, electronic-ink label 302 needs to be connected to both the last dose nut 240 (e.g., a moving location) and one end of the conductive track 721 (e.g., a stationary location). Therefore, an advantage of the track having two conductive elements connected together at one end of the track is that an electronic-ink label 302 need only be connected to one of the conductive elements at (i) a single location on the moving component (e.g., on the last dose nut 740 where the electronic-ink label 302 bridges the two conductive elements) or (ii) a single location along the track (e.g., at the end of the conductive track 721, where the last dose nut 740 bridges the conductive elements). In both cases, the position of the last dose nut 740 determines the overall length of the conductive elements in a circuit.

Embodiments of the present disclosure can also apply to prefilled single and double chamber syringes that may not use a cartridge. In some instances, the dose tracking mechanism is contained in the cartridge or in the drug delivery device in a manner enabling the dose tracking mechanism assembly to sense a change in the fill level of the cartridge or syringe after an injection. In some instances, components of the electronics assembly are located outside of the cartridge or in different parts of the cartridge or drug delivery device.

Some of the features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described embodiments by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about-4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des (B30) human insulin, B29-N-omega-carboxypentadecanoyl-gamma-L-glutamyl-des (B30)

human insulin (insulin degludec, Tresiba®); B29-N—(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

A number of embodiments of the present disclosure have been described. Nevertheless, it will be understood that various modifications may be made without departing from the spirit and scope of the present disclosure. Accordingly, other embodiments are within the scope of the following claims.

The invention claimed is:

1. An indication system for use in a drug delivery device, the indication system comprising:
 a housing;
 a moveable component configured to move with respect to the housing during operation of the drug delivery device;
 an electric circuit having an electrical property, the electric circuit comprising:
  an electrical component operatively coupled to the moveable component and configured to modify the electrical property based on a position of the moveable component, such that the electrical property of the electric circuit is an indication of the position of the moveable component, and
  an electric contact on an exterior of the housing; and
 an electronic-ink label configured to be disposed on the exterior of the housing, the electronic-ink label comprising:

printed electronics arranged to be in electrical communication with the electric circuit via the electric contact and configured to display a visual indication related to the position of the moveable component in response to the electrical property of the electric circuit, wherein the electrical component comprises:

a first component comprising:
    a track spanning at least a portion of a length of the first component, and
    first and second conductors, each extending continuously along an entire length of the track, the entire length spanning between a distal most end and a proximal most end of the track; and a second component that is conductive and moveable with respect to the first component along the track, the second component contacting the first and second conductors, wherein the electrical property is proportional to a position of the second component along the length of the first component, wherein the moveable component of the drug delivery device comprises the first component or the second component, and wherein the position of the second component with respect to the first component is changed during a dose setting operation or a dose dispensing operation of the drug delivery device.

2. The indication system of claim 1, wherein the moveable component is configured to move between a plurality of possible positions with respect to the housing, and wherein each of the plurality of possible positions of the moveable component defines a different value of the electrical property of the electric circuit, such that each value of the electrical property is an indication of a different position of the moveable component.

3. The indication system of claim 1, wherein the position of the moveable component corresponds to an amount of medicament inside a medicament container or a position of a stopper inside the medicament container.

4. The indication system of claim 1, wherein the electrical property is one or more of the following: capacitance, inductance, or resistance.

5. The indication system of claim 1, wherein the electronic-ink label comprises an outer surface configured to display the visual indication and an inner surface comprising corresponding electrical contacts arranged to contact the electrical contact of the housing, and wherein the inner surface is configured to be secured to the exterior of the housing via an adhesive.

6. The indication system of claim 1, comprising a dose memory mechanism having the moveable component, and wherein the position of the moveable component corresponds to a total dose of medicament remaining in the drug delivery device, and wherein the visual indication corresponds to the total dose of medicament remaining in the drug delivery device.

7. The indication system of claim 1, wherein the first component is a threaded sleeve configured to move helically with respect to the housing during a dose setting operation, and wherein the second component is a thread insert carried by the housing, wherein the moveable component is the threaded sleeve and the visual indication corresponds to a dose set during the dose setting operation.

8. The indication system of claim 1, wherein the first component is a leadscrew configured to move helically with respect to the housing during a dose dispensing operation of the drug delivery device to translate a stopper into a cartridge of the drug delivery device, wherein the second component comprises a bearing nut carried by the housing, and wherein the moveable component is the leadscrew and the visual indication corresponds to the position of the stopper in the cartridge.

9. The indication system of claim 1, wherein the first component is a threaded plunger rod, and the second component is a last dose nut configured to thread along a drive sleeve during the dose setting operation, and wherein the moveable component is the last dose nut and the visual indication corresponds to a dose remaining in the drug delivery device.

10. The indication system of claim 1, wherein the electronic-ink label comprises a battery for providing power to the printed electronics.

11. The indication system of claim 1, wherein the electronic-ink label comprises an outer surface comprising a display for showing the visual indication.

12. The indication system of claim 1, wherein the electronic-ink label comprises an RFID module configured to transmit a wireless signal related to the position of the moveable component in response to the electrical property of the electric circuit.

* * * * *